(12) United States Patent
Shackelford, Sr. et al.

(10) Patent No.: US 8,181,352 B1
(45) Date of Patent: May 22, 2012

(54) SCALPEL WITH REMOVABLE BLADE ASSEMBLY

(76) Inventors: Howard L. Shackelford, Sr., Triadelphia, WV (US); Howard L. Shackelford, Jr., Wheeling, WV (US)

( * ) Notice: Subject to any disclaimer, the term of this patent is extended or adjusted under 35 U.S.C. 154(b) by 752 days.

(21) Appl. No.: 12/326,944

(22) Filed: Dec. 3, 2008

(51) Int. Cl.
*B26B 1/08* (2006.01)
*A61B 17/3213* (2006.01)

(52) U.S. Cl. ............ 30/162; 30/335; 30/337; 30/339; 606/167

(58) Field of Classification Search ............ D24/146, D24/147; 606/167, 185; 30/162, 163, 335, 30/337, 339
See application file for complete search history.

(56) References Cited

U.S. PATENT DOCUMENTS

| | | | |
|---|---|---|---|
| 488,616 A | 12/1892 | Schott | |
| 990,882 A | 5/1911 | Krat | |
| 1,813,782 A | 7/1931 | Thompson | |
| 1,835,519 A | 12/1931 | Pauli | |
| 1,861,363 A | 5/1932 | Scheuner | |
| 2,316,985 A | 4/1943 | Niedermayer | |
| 2,350,121 A | 5/1944 | McCaskey | |
| 3,314,148 A * | 4/1967 | Foellmi | 30/162 |
| 3,708,881 A * | 1/1973 | Bennett | 30/335 |
| 3,905,101 A * | 9/1975 | Shepherd | 30/162 |
| 4,103,421 A | 8/1978 | Quenot | |
| D264,803 S | 6/1982 | Machida | |
| 4,575,940 A | 3/1986 | Wenzel | |
| 4,615,118 A | 10/1986 | Ihata | |
| 5,139,507 A * | 8/1992 | Dolgin et al. | 606/167 |
| 5,299,357 A | 4/1994 | Wonderley et al. | |
| 5,481,804 A | 1/1996 | Platts | |
| 5,531,754 A * | 7/1996 | Shackelford et al. | 606/167 |
| 6,015,419 A * | 1/2000 | Strome et al. | 606/167 |
| 6,254,621 B1 | 7/2001 | Shackelford et al. | |
| 6,510,612 B1 * | 1/2003 | Cybulski | 30/162 |
| D483,871 S * | 12/2003 | Endo | D24/147 |
| 6,745,474 B1 * | 6/2004 | Huang | 30/162 |
| 6,865,816 B1 | 3/2005 | Zajdel | |
| 7,101,382 B2 * | 9/2006 | George et al. | 606/167 |
| 7,314,471 B2 * | 1/2008 | Holman | 606/167 |
| 7,434,317 B2 * | 10/2008 | Levine et al. | 30/162 |
| 7,647,704 B2 * | 1/2010 | Petersen | 30/339 |
| 7,810,241 B2 * | 10/2010 | Pooler | 606/167 |
| 7,857,824 B2 * | 12/2010 | Kiehne | 606/167 |
| 8,015,712 B2 * | 9/2011 | Yi et al. | 30/162 |
| 2002/0096032 A1 | 7/2002 | Peyrot et al. | |
| 2003/0200661 A1 * | 10/2003 | Okada | 30/162 |
| 2006/0041265 A1 * | 2/2006 | Shackelford, Sr. | 606/167 |
| 2006/0149300 A1 * | 7/2006 | Jessen et al. | 606/167 |

(Continued)

FOREIGN PATENT DOCUMENTS

WO    WO 9735525 A1 * 10/1997

(Continued)

*Primary Examiner* — Jason Daniel Prone
(74) *Attorney, Agent, or Firm* — Eckert Seamans Cherin & Mellott, LLC; David C. Jenkins

(57) ABSTRACT

A surgical blade device similar to a disposable scalpel wherein the blade assembly is easily replaceable is provided. The surgical blade device allows the user to replace a blade assembly during surgery or, after sterilization of the handle and replacement of the blade assembly, reuse the surgical blade device. The surgical blade device disclosed herein further provides for an inexpensive blade assembly replacement device which is simple to operate. That is, the blade replacement device has a limited number of components.

19 Claims, 9 Drawing Sheets

U.S. PATENT DOCUMENTS

| | | | |
|---|---|---|---|
| 2010/0036404 A1* | 2/2010 | Yi et al. | 606/167 |
| 2010/0063522 A1* | 3/2010 | Reaux | 606/167 |
| 2010/0152755 A1* | 6/2010 | Kehr et al. | 606/167 |
| 2011/0083326 A1* | 4/2011 | Sullivan | 30/162 |
| 2011/0270291 A1* | 11/2011 | Nakamura | 606/167 |

FOREIGN PATENT DOCUMENTS

| | | |
|---|---|---|
| WO | WO 2010065508 A1 * | 6/2010 |

\* cited by examiner

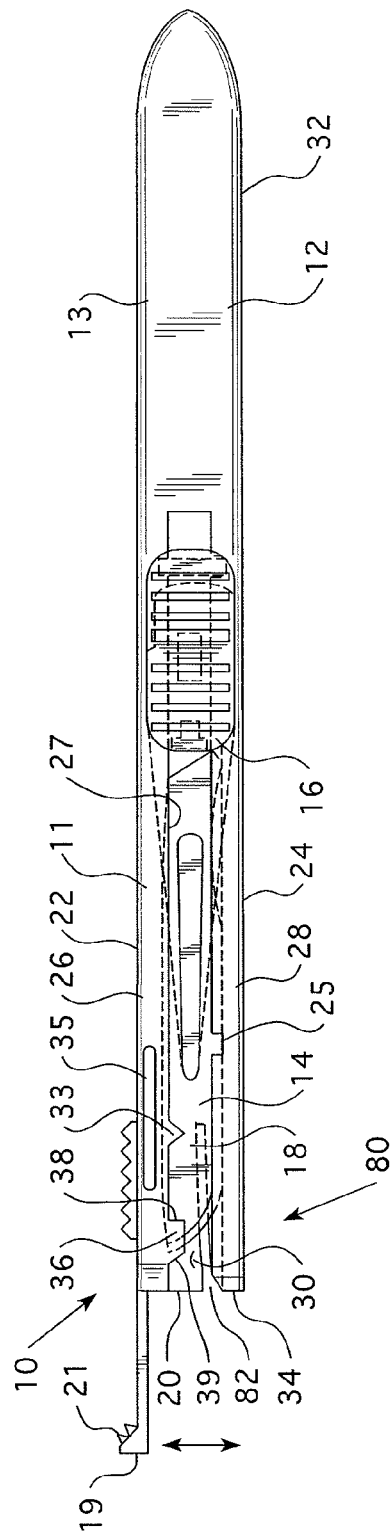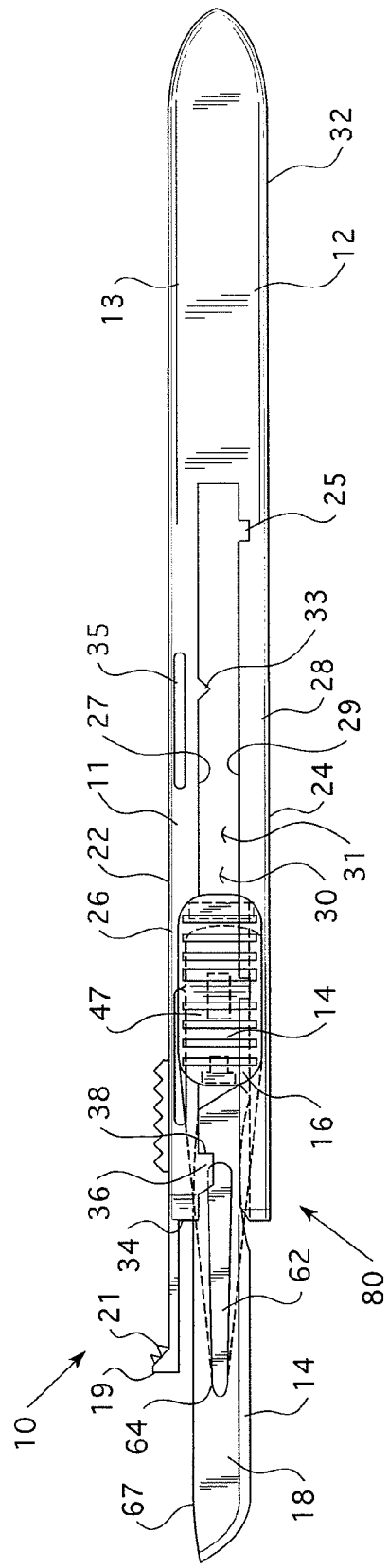
FIG. 1
FIG. 2

SCALPEL WITH REMOVABLE BLADE ASSEMBLY

BACKGROUND OF THE INVENTION

1. Field of the Invention

This invention relates to a retractable surgical blade device and an associated method and, more specifically, to a retractable surgical blade device having a removable blade assembly.

2. Background Information

Traditional surgical scalpels are well known devices used by surgeons and other medical personnel to make incisions into patients or for the purpose of dissection. Scalpels are specialized knives typically consisting of a handle member and a removable surgical blade disposed on one end of the handle. The surgical blades, in order to be effective, are extremely sharp and must be handled carefully by all personnel involved in the surgical procedure in which the scalpel is used.

Because the traditional scalpels have exposed blades, the chance of accidental stabbing or cutting of medical personnel is great. In addition to the injury caused by the cut or stab itself, infectious viruses and/or bacteria can enter into the cut or wound during the surgical procedure. Many infectious diseases can be transmitted between the blood of a surgical patient and an open wound of medical personnel inadvertently cut by the surgical blade of a scalpel.

Medical personnel may be protected from accidental scalpel wounds by a retractable surgical blade device such as the ones disclosed in U.S. Pat. Nos. 5,531,754 and 6,254,621 which are incorporated by reference. The retractable surgical blade device includes a handle and a blade assembly. The handle defines a channel. The blade assembly includes a blade on a body member, or slider. The blade assembly is structured to be movably disposed within the handle channel. The front end of the channel includes a stop which allows the blade to be extended therefrom while preventing the slider from passing therethrough. Thus, medical personnel may move the blade assembly between a first, withdrawn position, wherein the blade is disposed within the channel, and a second, cutting position, wherein the blade extends from the channel. These designs for "safety scalpels" present an elegant solution to the problem of exposed blades during surgery.

Such safety scalpels typically include a plastic handle and a blade assembly, that is, a plastic slider with an attached steel blade. With these materials, safety scalpels are relatively inexpensive and were intended to be disposable after use on a single patient; however, as the cost of medical devices in general continue to increase, many health care organizations are looking to cut costs wherever possible and are attempting to find ways to reuse such safety scalpels. Further, plastic scalpels tend to be relatively light weight and lack the heft of metal scalpels. Many surgeons prefer a scalpel that has heft.

One solution to these problems is to provide a metal handle, typically stainless steel, into which a disposable blade assembly may be inserted. The metal handle provides a desired heft and replacing the blade assembly is less expensive than disposing the entire scalpel. However, the blade assembly replacement devices presently utilized have complicated mechanisms structured to selectively hold or release the blade assembly. Such complicated devices have multiple areas, colloquially called "nooks and crannies," in which blood, or even small pieces of flesh, may become trapped. When biological material becomes trapped in the scalpel handle, sterilization becomes difficult, if not impossible.

SUMMARY OF THE INVENTION

The concept disclosed and claimed herein provides for a scalpel similar to a disposable scalpel wherein the blade assembly is easily replaceable. Such a scalpel allows the user to replace a blade assembly during surgery or, after sterilization of the handle and replacement of the blade assembly, reuse the scalpel. The scalpel concept disclosed herein further provides for an inexpensive blade assembly release device having few components and which is simple to operate.

Generally, the concept provides a safety scalpel wherein a blocking member, or stop, which prevents forward motion of the blade assembly beyond the handle channel, is disposed upon the upper side of a gap through which a portion of the slider travels. The side walls defining the lower side of the gap are structured to be moved between a first position, wherein the gap is too narrow for the slider to pass, and a second position, wherein the gap is wide enough to allow the slider to pass the stop. Alternately, the back end of the channel may be open and the user may insert the new blade assembly via the open channel. In this alternate embodiment, the channel includes at least one, and preferably a plurality of stops or other locking devices that prevent the blade assembly from accidentally being removed via the channel back end.

The blade assembly may be inserted, via the front end or the back end of the channel, by hand. However, in a preferred embodiment, a blade assembly support device supports and positions one or more blades so that a user may install the blade assembly merely by pressing the handle into a blade compartment. That is, each blade compartment supports a blade assembly in a manner that allows the handle to be moved onto the blade assembly until the blade assembly is inserted within the channel.

To remove the blade assembly, the user may use a fixed surface, such as, but not limited to, an edge of a blade assembly receptacle, to engage the upper edge of the blade. When the upper edge of the blade is biased toward the lower side of the channel, i.e. when the blade upper edge is pushed against the fixed surface, the lower side of the channel is moved into the second position. At this point, the user may move the slider past the blocking member and allow the blade assembly to fall into the receptacle. Alternately, the handle may include a forward extension that protrudes over the blade when the blade is in the second position. The forward extension is flexible and allows the user to bias the upper edge of the blade toward the lower side of the channel without having the user touch the blade assembly.

The blade assembly, and more specifically the portion of the slider structured to be disposed with the channel, is configured to move the lower side of the channel into the second position during blade assembly insertion. That is, the back side of the blade assembly slider channel portion is shaped as a wedge having the narrow end at the back edge of the slider. In this configuration, when a user begins to insert a new blade assembly, the wedge-shaped portion of the slider causes the lower side of the channel to move into the second position. Preferably, new blade assemblies are stored in a "feeder" device that presents the back side of a single new blade assembly. The feeder has a storage bin and a coupling bay. The back side of a single new blade assembly is exposed in the coupling bay. When the exposed blade assembly is removed, a new blade assembly is moved, typically by gravity, from the bin into the coupling bay.

BRIEF DESCRIPTION OF THE DRAWINGS

A full understanding of the invention can be gained from the following description of the preferred embodiments when read in conjunction with the accompanying drawings in which:

FIG. 1 is a side view of the retractable surgical blade device with the blade assembly in the withdrawn position.

FIG. 2 is a side view of the retractable surgical blade device with the blade assembly in the cutting position.

DESCRIPTION OF THE PREFERRED EMBODIMENTS

As used herein, directional descriptors such as, but not limited to, "front," "back," "forward," and "rear" assume that the end of the closed channel retractable surgical blade device 10 from which the blade assembly 14 extends is the "front" end of the handle member 12.

Figure 3:
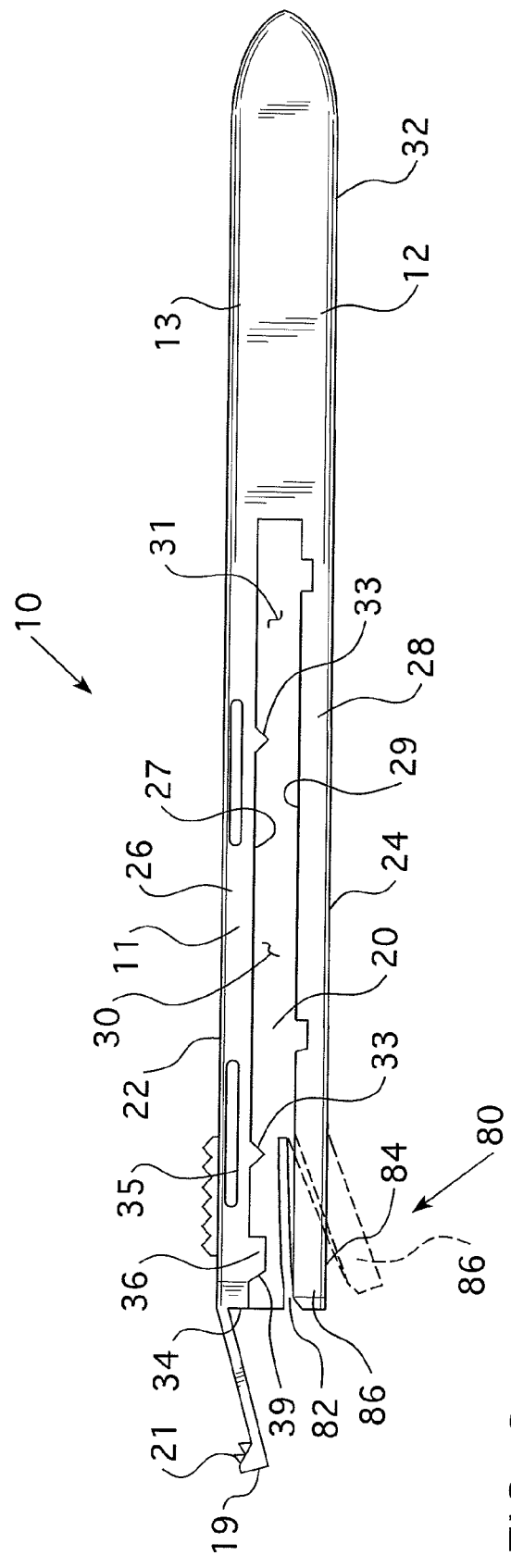
FIG. 3 is a side view of the handle assembly with the blade assembly removed and showing the second sidewall front end portion and said second flange front end portion in a first position in solid line and the second position in ghost. It is noted that the second position of the second sidewall front end portion and said second flange front end portion is greatly exaggerated for visibility.

As shown in FIG. 1, a scalpel blade replacement system includes a surgical blade device 10 and at least one blade assembly container 200. The surgical blade device 10, shown in FIGS. 1-3, is a retractable surgical blade device 10 that includes a handle member 12 and a surgical blade assembly 14. The handle member 12 has two portions: a front portion 11 and a back portion 13. The surgical blade assembly 14 consists of a slider 16 to which a unitary surgical blade 18 is removably secured. The surgical blade assembly 14 is adapted for slidable movement in the handle member 12 and, more specifically, the handle member front portion 11. That is, the blade assembly 14 may be moved between at least two positions in the handle member 12; a first, withdrawn position, wherein the blade assembly 14 is disposed within the handle and the blade 18 (discussed below) is not exposed; and a second, cutting position, wherein the blade assembly 14 is disposed at the front end 34 (discussed below) and the blade 18 is substantially exposed.

The surgical blade device 10 further includes a slider replacement assembly 80. It is noted that some users may replace the slider 16 and then attach a surgical blade 18 thereto. More typically, however, the slider replacement assembly 80 is structured to allow a user to easily replace the blade assembly 14 and thereby allow the use of a new surgical blade 18. The slider replacement assembly 80 relies upon the interaction of various components incorporated into the handle member front portion 11 and the slider 16. That is, the slider replacement assembly 80 is not a discrete assembly or element. Accordingly, the components of the slider replacement assembly 80 will hereinafter be described in conjunction with other components on related elements. For example, the stop 36, discussed below, will be described in conjunction with the handle member 12 as the stop 36 is disposed upon the handle member 12 and also serves functions not related to the slider replacement assembly 80. Following the description of the components of the retractable surgical blade device 10, the operation of the slider replacement assembly 80 will be described. It is noted that the following components are, or may be, part of the slider replacement assembly 80: the stop 36, the slider interconnecting intermediate portion 44, the hinge slot 82, the second sidewall front end portion 84 and the second flange front end portion 86.

Figure 6:
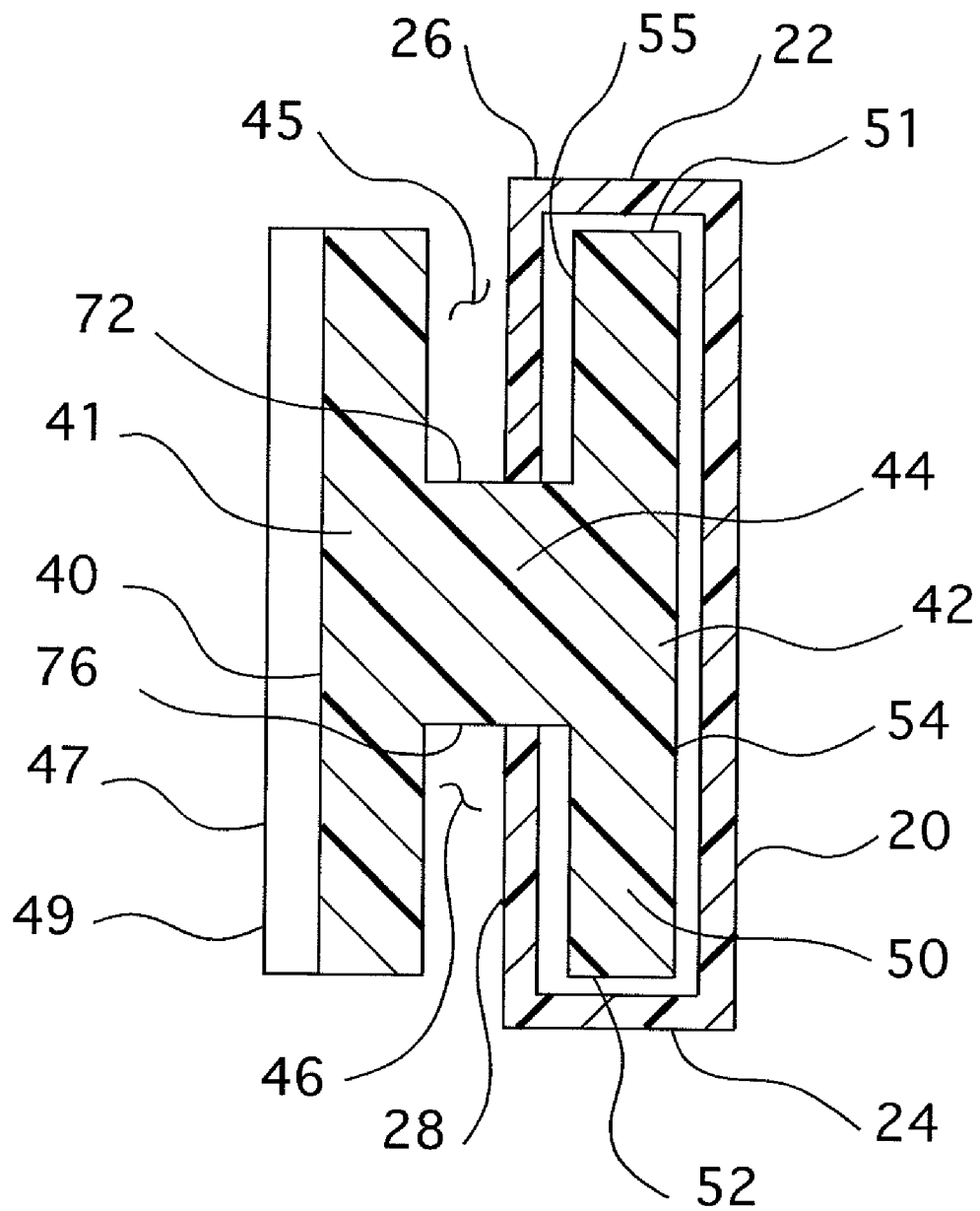
FIG. 6 is a cross-sectional view of the blade assembly disposed in the handle member.
Figure 7:
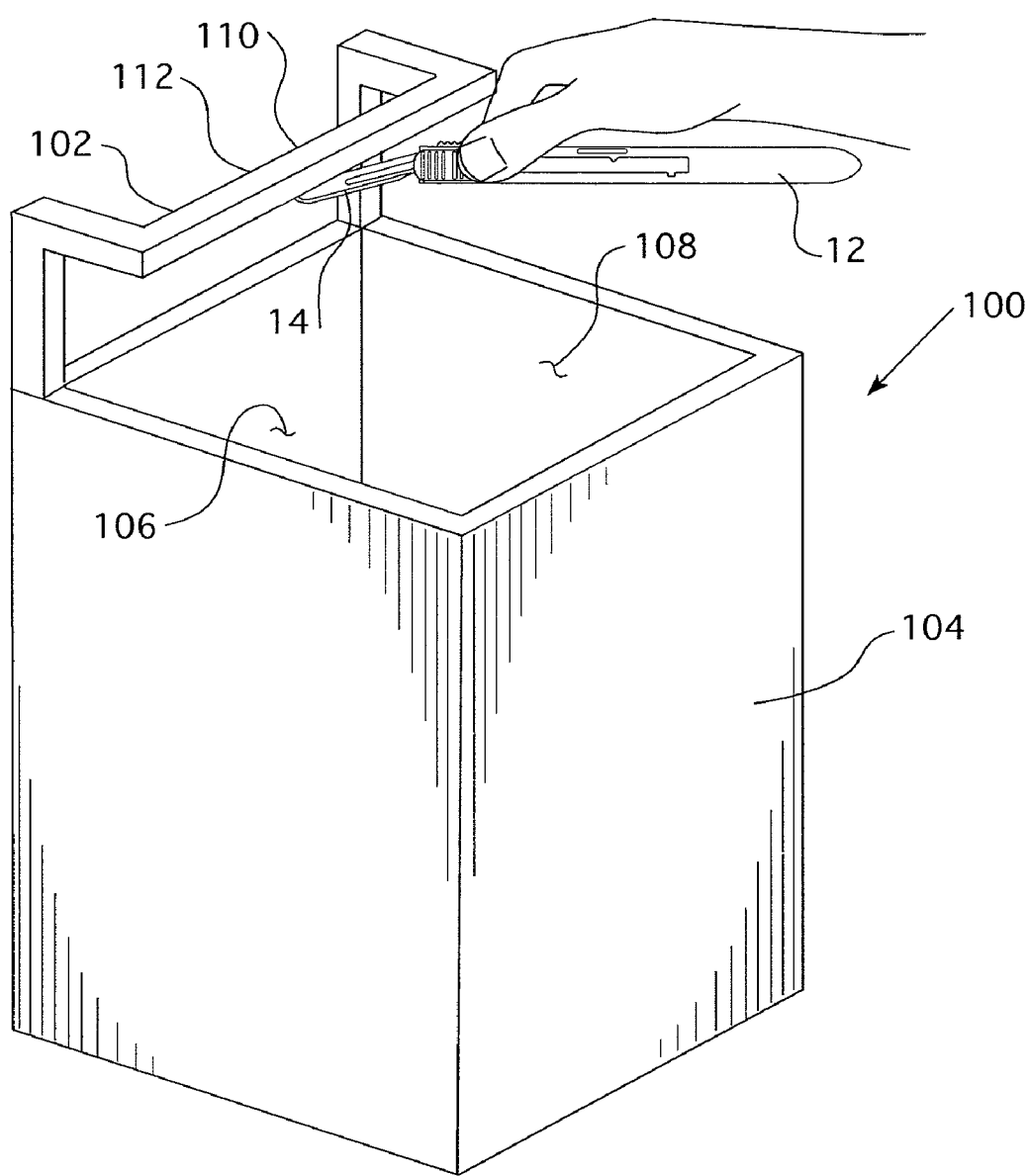
FIG. 7 is an isometric view of a receptacle.

The handle member 12 is, preferably, made from stainless steel. This allows the handle member 12 to be sterilized using traditional methods and provides a scalpel 10 with heft as many surgeons prefer. Further, stainless steel allows for the flexibility required for the slider replacement assembly 80, as described below. The handle member 12 front portion 11 consists of a base wall 20, two elongated generally parallel longitudinal sidewalls 22, 24, as shown, a first, upper side wall 22 and second, lower sidewall 24, and two elongated longitudinal flanges 26, 28, a first and second flange, respectively. The sidewalls 22, 24 extend generally perpendicular from the longitudinal edges of the base wall 20. Each flange 26 and 28 extends generally perpendicularly from the longitudinal edges of one of the sidewalls 22, 24 and over the base wall 20. In this configuration, the handle member front portion 11 generally defines a longitudinal channel 30 having a cross-section shape not unlike a "C" formed from straight members at generally right angles, as shown in FIG. 6 (discussed below). The handle member front portion 11, therefore, defines a channel 30 in which the surgical blade assembly 14 is slidably movable.

Further, the first and second flanges 26, 28 each have a distal interior edge 27, 29 opposite sidewalls 22 and 24, respectively. There is a gap 31 between the flange distal interior edges 27, 29. It is noted that, while not part of this invention, just within one or more of the flange distal interior edges 27, 29 an axially extending hollow 35 may exist. On a flange distal interior edge 27, 29 along the length of the hollow 35, an inwardly extending positioning tooth 33 may exist. Such a tooth 33 engages the slider 16 and, more specifically, engages a detent on the slider body 40, discussed below. Thus, the positioning tooth 33 may assist in holding the slider 16, and therefore the blade assembly 14, in a predetermined location such as, but not limited to, a cutting position or a withdrawn position.

The handle member back portion 13 also includes the base wall 20 and the two elongated generally parallel longitudinal sidewalls 22 and 24 which extend generally perpendicularly from the longitudinal edges of the base wall 20, as well as a front wall 32. Front wall 32 extends between sidewalls 22 and 24 in a plane generally parallel to base wall 20. The back portion front wall 32 may be joined with or integral to base wall 20. That is, the handle member back portion 13 is generally solid and the channel 30 is closed off. In an alternate embodiment, shown in FIG. 8 and discussed below, the channel 30 extends through the handle member back portion 13 and is open at the handle member back portion 13. As is known in the art, when the channel 30 extends through the handle member back portion 13, there are a number of notches that act as a lock 25 to prevent the surgical blade assembly 14 from accidentally being removed via the handle member back portion 13. That is, each lock 25 cooperates with a tab (not shown) or similar structure incorporated into the slider 16. The tab is biased away from the base wall 20 and, when the slider is positioned at a lock 25, the tab is biased into the lock. When the tab is in the lock, the slider 16 cannot be moved axially in the channel. To free the slider 16, the user must overcome the bias of the tab and move the tab out of the lock 25. This is typically accomplished by pressing the grip 49 (discussed below) toward the base wall 20.

The handle member front portion 11 has a front end 34 which is open. That is, the channel 30 opens through the handle member front portion front end 34. At the handle member front portion front end 34, at least one, and as shown the upper flange distal interior edge 27, includes a stop 36. The stop 36 is disposed adjacent to, or at, the handle member front portion front end 34. The stop 36 is an extension into the flange gap 31 and, as such, the stop 36 significantly narrows the flange gap 31. The stop 36 has a inner edge 38 and a outer edge 39. The stop inner edge 38 extends generally perpendicular to the upper flange distal interior edge 27. The stop outer edge 39 is a wedge with the narrow end disposed closer to the handle member front portion front end 34. As discussed below, the slider body intermediate portion 44 travels through the flange gap 31. Thus, at the location of the stop 36, the flange gap 31 is too narrow for the slider body intermediate portion 44 to pass therethrough, except as discussed below.

The handle base wall 20 includes a hinge slot 82 extending from the handle member front portion front end 34 rearwardly. The hinge slot 82 is, preferably, disposed adjacent to, and extending generally along, the second lower sidewall 24. The portions of the second lower sidewall 24, as well as the second flange 28, disposed immediately adjacent to the hinge slot 82 are the second sidewall front end portion 84 and said second flange front end portion 86. As described below, the hinge slot 82 is structured to allow the second sidewall front end portion 84 and said second flange front end portion 86 to flex away from the longitudinal axis of the handle member 12.

The handle member front portion 11, and more specifically the upper side wall 22, may include an extension 19. The extension 19 is, essentially, a continuation of the upper side wall 22 that protrudes from the handle member front portion 11 in a direction generally parallel to the longitudinal axis of the handle member 12. In this configuration, the extension 19 is a cantilever that extends over the path of travel of the blade assembly 14. The extension 19 may include a finger stop 21, which is a vertically extending tab 21. The extension 19 may be flexed downwardly toward the path of travel of the blade assembly 14. When the extension 19 is flexed downwardly, and when the blade assembly 14 is in the second, cutting position, the second sidewall front end portion 84 and the second flange front end portion 86 move into a second position, as described below.

Figure 4:
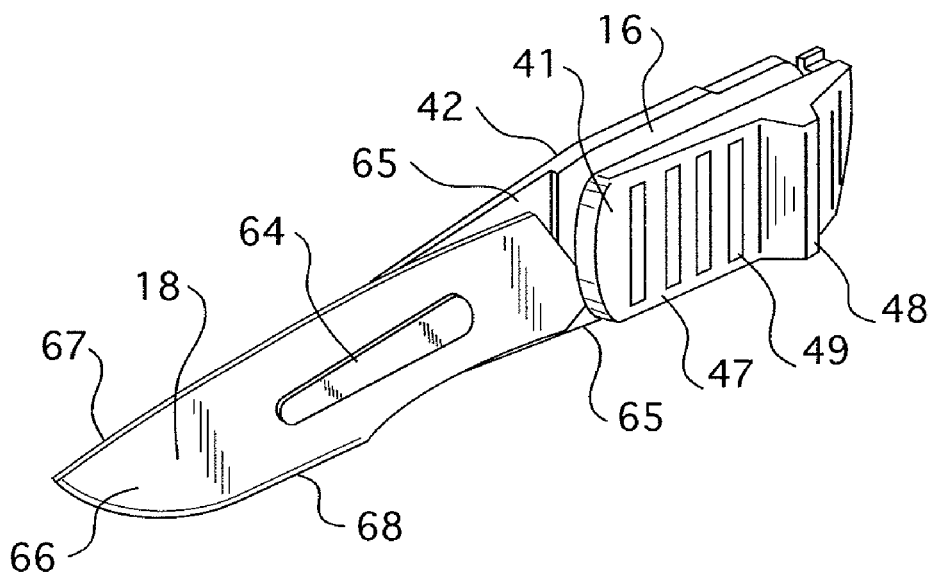
FIG. 4 is an isometric view of the blade assembly.
Figure 5:
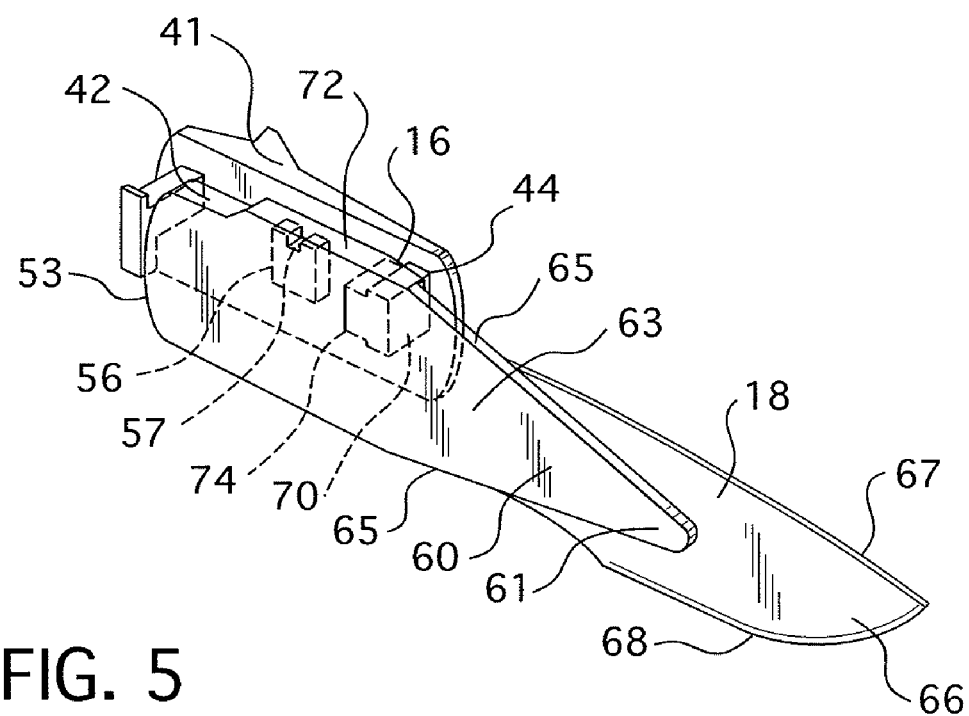
FIG. 5 is another isometric view of the blade assembly from a different perspective.

As noted above, the surgical blade assembly 14 consists of a slider 16 to which a unitary surgical blade 18 is removably secured. The slider 16 is shown in FIGS. 4-6. The slider 16 includes a body 40 and a projection 60. As can best be seen in FIG. 5, the center portion of the slider body 40 has a cross-sectional shape similar to an "I-beam" (FIG. 6) consisting of a generally rectangular first portion 41, a generally rectangular second portion 42 and an interconnecting intermediate portion 44. The slider body 40 shape defines opposed first and second longitudinal slots 45, 46. When the slider 16 is disposed within the handle channel 30, flanges 26 and 28 engage into slots 45, 46, respectively and cooperate to guide and maintain the blade assembly 14 in the channel 30. That is, when the blade assembly 14 is coupled to the handle member 12 the slider body second portion 42, and more specifically the channel member 50 (discussed below), is disposed in the channel 30, while first portion 41 is disposed external to the channel 30. Thus, the slider body intermediate portion 44 travels through the flange gap 31.

In this configuration, the slider body first portion 41 may be elongated in an axial direction, i.e. the direction of travel of the slider 16, to form a grip 49. The grip 49 facilitates engaging and moving the surgical blade assembly 14 in the channel 30. The grip 49 includes an engaging surface 47 which, preferably, has a central ridge 48 that further enhances the users engagement of the slider 16. That is, the central ridge 48 provides a surface for the user to push or pull against when moving the slider 16.

The slider body second portion 42 is also elongated in the axial direction and includes a channel member 50 and the slider projection 60. The channel member 50 is the section of the slider body second portion 42 that extends rearwardly of the intermediate portion 44. The channel member 50 is, preferably, a generally flat planar member having a thickness slightly less than the thickness of the channel 30. Thus, when the channel member 50 is disposed in the channel 30, the channel member 50 is loose enough to slide easily, but thick enough so that the slider 16 maintains an orientation substantially parallel to the plane of the channel 30. That is, the channel member 50 is structured to resist "wobbling" while disposed within the channel 30. It is further noted that the gaps between the channel member 50 and the handle member sidewalls 22, 24 and flanges 26, 28 are exaggerated as shown in FIG. 6. The channel member 50 has an upper side 51, a lower side 52, a back side 53, an inward face 54, and an outward face 55. The intermediate portion 44 is coupled to the outward face 55. When the channel member 50 is disposed in the channel 30, the inward face 54 engages the handle member base wall 20. The channel member outward face 55 may also include a positioning mount 56. The positioning mount 56 is a construct that, when the slider 16 is disposed in the channel 30, extends into the flange gap 31. The positioning mount 56 defines a detent 57 which is structured to be engaged by the positioning tooth 33 that extends from the upper flange distal interior edge 27 (as shown).

The slider projection 60 is the section of the slider body second portion 42 that extends generally forward of the intermediate portion 44. Thus, the slider projection 60 has a distal end (tip) 61 and a proximal end 63. The slider projection proximal end 63 is directly coupled to, or may be formed as a unitary body with, the slider body second portion 42. The slider projection 60 also includes a blade mount 62 that is structured to be coupled to a surgical blade 18. That is, the surgical blade 18 is secured to the slider projection 60 as can best be seen in FIG. 2. The surgical blade 18 defines an aperture 64 which is disposed over, and preferably fixed to, blade mount 62 disposed on slider projection 60. Preferably, the slider projection proximal end 63 has a greater height than the surgical blade 18 at the slider projection proximal end 63. Further, the surgical blade 18 is preferably centered on the slider projection 60 so that, at the slider projection proximal end 63, the slider projection 60 extends beyond the surgical blade 18 on both the upper and lower sides of the surgical blade 18. In this configuration, the portion of the slider projection proximal end 63 that extend beyond the surgical blade 18 are identified as "hips" 65.

The slider body intermediate portion 44 includes a front face 70, an upper face 72, a rearward extension 74 and a lower face 76. The slider body intermediate portion upper face 72 and lower face 76 are generally parallel to each other and both extend generally in an axial direction. The slider body intermediate portion front face 70 extends generally perpendicular to, and between, the slider body intermediate portion upper face 72 and lower face 76. The slider body intermediate portion 44 may include a generally flat rear face (not shown) that is generally parallel to the slider body intermediate portion front face 70, however, the slider body intermediate portion 44 may have a wedge-like rearward extension 74. That is, the rearward extension 74 tapers axially in a rearward direction.

The surgical blade 18 is a thin, elongated body 66 having a blunt upper edge 67 opposite a sharp cutting edge 68. As noted above, the surgical blade 18 defines an aperture 64 which is disposed over, and preferably removably coupled to, the slider blade mount 62. It is noted that the surgical blade aperture 64 is preferably structured to allow the blade 18 to be removed from the slider blade mount 62. Thus, surgeons, who are known to have preferred blade manufacturers, may have their preferred brand of blades 18 coupled to each slider 16.

When the slider 16 is disposed within the handle channel 30, the slider body intermediate portion upper face 72 engages, or is immediately adjacent to, the upper flange distal interior edge 27. Similarly, when the slider 16 is disposed within the handle channel 30, the slider body intermediate portion lower face 76 engages, or is immediately adjacent to, the lower flange distal interior edge 29. In this configuration, the slider 16 and therefore the surgical blade assembly 14, is structured to move between the first, withdrawn position, wherein the surgical blade 18 is disposed within the channel 30, and the second, cutting position, wherein the surgical blade 18 extends beyond the handle front end 34 and may be used for cutting.

It is noted that, when the slider 16 is moved to the handle front end 34, the slider body intermediate portion front face 70 contacts the handle stop inner edge 38. The handle stop inner edge 38 and the slider body intermediate portion front face 70 are generally parallel to each other and, as such, will not slide over each other when brought into contact. Accordingly, the handle stop inner edge 38 effectively prevents the slider 16 from moving past the channel 30 opening at the handle front end 34, except as discussed below.

In this configuration, and as shown in FIG. 3, the slider replacement assembly 80 is operable as follows. The slider replacement assembly 80 is structured to allow the second sidewall front end portion 84 and the second flange front end portion 86 to move between a first position, wherein the second sidewall front end portion 84 extends generally parallel to the first sidewall 22 and the second flange front end portion 86 extends generally parallel to the first flange 26, and a second position, wherein the second sidewall front end portion 84 is angled away from the first sidewall 22 and the second flange front end portion 86 is angled away from to the first flange 26, thereby increasing the width of the flange gap 31 at the handle front end 34. As noted above, when the second sidewall front end portion 84 and the second flange front end portion 86 are in the normal first position, the flange gap 31 at the location of the stop 36 is too narrow for the slider body intermediate portion 44 to pass therethrough; however, when the second sidewall front end portion 84 and the second flange front end portion 86 are in the second position, wherein the flange gap 31 is wider, the slider body intermediate portion 44 may pass the stop 36 and the slider 16, and therefore the blade assembly 14, may exit the channel 30. Thus, the blade assembly 14 is removable.

It is noted that the blade assembly 14 may be removed with one hand. That is, a user may position the blade assembly 14 in the cutting position, wherein the slider 16 is moved to the handle front end 34 and the blade 18 extends from the channel 30. The user may then apply pressure, that is, a biasing force, to the blunt blade upper edge 67. If the handle has an extension 19, the user may apply pressure to the extension 19 which in turn acts upon the blade upper edge 67. This force causes the slider 16 to be biased downwardly which, in turn, causes the second sidewall front end portion 84 and the second flange front end portion 86 to move into the second position. When the second sidewall front end portion 84 and the second flange front end portion 86 are in the second position, the user applies a forward bias to the slider grip 49 causing the slider 16, and therefore the blade assembly 14, to exit the channel 30. It is noted that, unless the blade assembly 14 is being held, the blade assembly 14 will fall away at this point. Thus, a typical user will eject the blade assembly 14 over a biohazard waste container.

Alternately, a disposal receptacle 100 having an ejection device 102 may be used. The receptacle 100 has a body 104 defining an enclosed space 106 with an upper opening 108. The ejection device 102 may include a fixed generally horizontal member 110, such as, but not limited to a rod 112, disposed over the upper opening 108. With the blade assembly 14 in the cutting position, the user may bias the blade blunt upper edge 19 against the horizontal member 110, and apply a forward bias to the slider grip 49 causing the slider 16, and therefore the blade assembly 14, to exit the channel 30. At this point, the blade assembly 14 will fall into the disposal receptacle 100 through the upper opening 108.

Insertion of a new blade assembly 14 is accomplished by moving a blade assembly 14, and more specifically the slider body second portion 42, into the channel 30. In the embodiment of the handle member 12 having a solid handle member back portion 13, the blade assembly 14 insertion must occur at the handle member front end 34. If the handle member 12 has an open back portion 13, blade assembly 14 insertion may occur via the open back portion 13, as discussed below. Blade assembly 14 insertion at the handle member front end 34 is accomplished as follows. The blade assembly 14 is positioned at the handle member front end 34 with the slider body second portion 42 positioned in front of the channel 30 and the slider body intermediate portion 44 positioned in front of the flange gap 31. The user then moves the blade assembly 14 rearwardly relative to the handle member 12. As the blade assembly 14 moves into the channel 30, the slider body intermediate portion 44 moves into the flange gap 31. Once the slider body intermediate portion 44 engages the wedge-shaped stop outer edge 39, any additional rearward movement of the blade assembly 14 causes the wedge-shaped stop outer edge 39 to apply a biasing force to the slider body intermediate portion upper face 72. This bias is transferred through the slider body intermediate portion 44 which is also contacting the second flange front end portion 86. Thus, the downward bias causes the second sidewall front end portion 84 and the second flange front end portion 86 to move into the second position, thereby allowing the slider body intermediate portion 44 to move past the stop 36. Once the slider body intermediate portion 44 is past the stop 36, the second sidewall front end portion 84 and the second flange front end portion 86 return to the first position and the new blade assembly 14 is captured within the channel 30. Once the new blade assembly 14 is captured within the channel 30, the new blade assembly 14 is, preferably, moved to the withdrawn position until it is needed. It is noted that the slider body intermediate portion rearward extension 74 may also be shaped as a wedge shape and structured to engage the stop outer edge 39.

Figure 8:
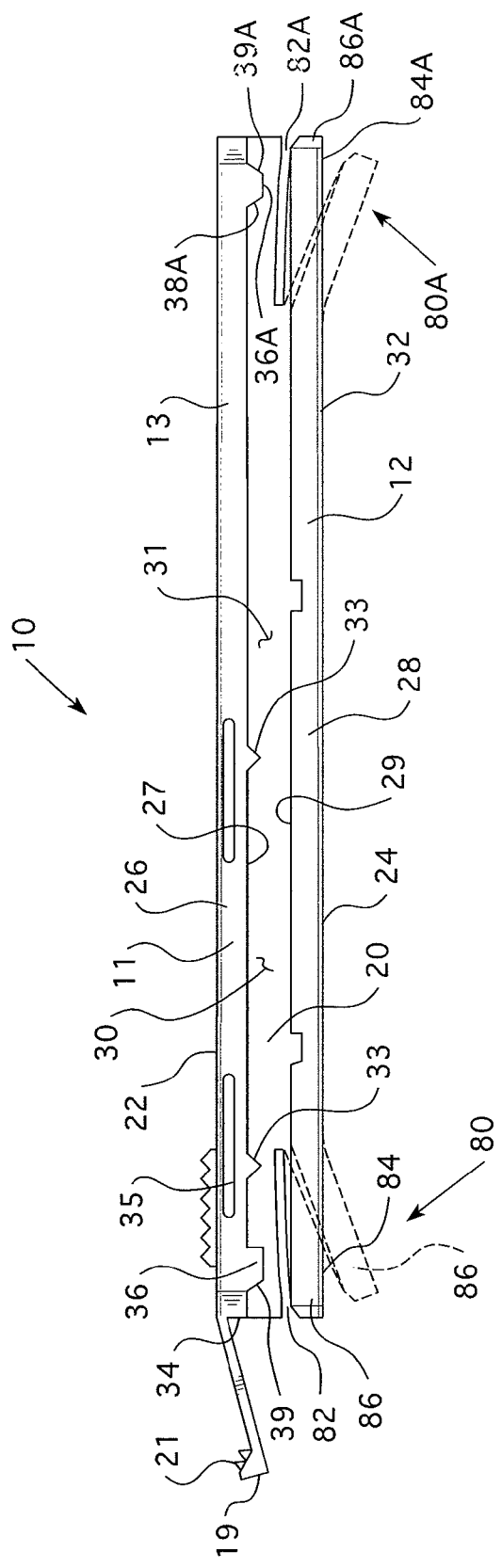
FIG. 8 is a side view of an alternate embodiment of the retractable surgical blade device with the blade assembly removed and showing the second sidewall front end portion and said second flange front end portion in a first position in solid line and the second position in ghost. It is noted that the second position of the second sidewall front end portion and said second flange front end portion is greatly exaggerated for visibility.

In an alternate embodiment, the surgical blade device 10, and more specifically the handle member 12, has an open back portion 13 as shown in FIG. 8. That is, in this embodiment the channel 30 extends the entire length of the handle member 12. Thus, the elements set forth above, namely the base wall 20, two elongated generally parallel longitudinal sidewalls 22, 24, the first, upper side wall 22 and second, lower sidewall 24, and the two elongated longitudinal flanges 26, 28, extend over the back portion 13 as well as the front portion 11. Further, the back portion 13 may also include a second, slider replacement assembly 80A. Other than the ramp 36A detailed below, the elements of the back portion slider replacement assembly 80A are substantially similar to the elements of the front portion slider replacement assembly 80 described above and shall use similar reference numbers followed by the letter "A." Further, descriptions using the word "front" shall, for the back portion slider replacement assembly 80A, use the word "back."

While still similar, one notable difference between the back portion slider replacement assembly 80A and the front portion slider replacement assembly 80 is that, in the back portion slider replacement assembly 80A, there is no need for a stop 36. That is, while the back portion slider replacement assembly 80A allows for the replacement of a surgical blade assembly 14, because the surgical blade assembly 14 exits the channel 30 slider 16 first, there cannot be the equivalent of a cutting position for the surgical blade assembly 14. As there is no cutting position associated with the back portion slider replacement assembly 80A, there is no need for a stop 36.

Further, it is noted that the procedure for the removal of a surgical blade assembly 14 described above positions the blade assembly 14 in the cutting position prior to removal, i.e. with the blade extending from the channel 30 so that the user may bias the blunt blade upper edge 67. As there is no cutting position associated with the back portion slider replacement assembly 80A, there is not a significant portion of the blade assembly 14 that is available for the user to bias the blade assembly downwardly when the blade assembly 14 is at the channel opening of the handle member back portion 13. Thus, to open the back portion slider replacement assembly 80A, an inner ramp 36A is used instead of the stop 36 of the front portion slider replacement assembly 80.

Thus, the elements of the back portion slider replacement assembly 80A include a ramp 36A, a slider interconnecting intermediate portion 44, a hinge slot 82A, second sidewall back end portion 84A and a second flange back end portion 86A. The ramp 36A is disposed at the back end of the handle member back portion 13. The ramp 36A is an extension into the flange gap 31 and, as such, the ramp 36A significantly narrows the flange gap 31. The ramp 36A has an inner edge 38A and an outer edge 39A. The ramp inner edge 38A is a wedge with the narrow end disposed closer to the middle of the handle member 12. The ramp outer edge 39A is a wedge with the narrow end disposed at the back end of the handle member back portion 13. As discussed above, the slider body intermediate portion 44 travels through the flange gap 31. Thus, at the location of the ramp 36A, the flange gap 31 is too narrow for the slider body intermediate portion 44 to pass therethrough, except as discussed below.

The handle base wall 20 includes a hinge slot 82A extending from the back end of the handle member back portion 13 forwardly. The hinge slot 82A is, preferably, disposed adjacent to, and extending generally along, the second lower sidewall 24. The portions of the second lower sidewall 24, as well as the second flange 28, disposed immediately adjacent to the hinge slot 82A are the second sidewall back end portion 84A and the second flange back end portion 86A. As described below, the hinge slot 82A is structured to allow the second sidewall back end portion 84A and said second flange back end portion 86A to flex away from the longitudinal axis of the handle member 12.

As before, when the slider 16 is disposed within the handle channel 30, the slider body intermediate portion upper face 72 engages, or is immediately adjacent to, the upper flange distal interior edge 27, and, the slider body intermediate portion lower face 76 engages, or is immediately adjacent to, the lower flange distal interior edge 29. However, because the back portion slider replacement assembly 80A includes a ramp 36A rather than a stop 38, when the blade assembly 14 is moved rearwardly in the channel 30, the slider body intermediate portion upper face 72 engages the wedge-like ramp inner edge 38A. Further rearward movement of the blade assembly 14 causes the wedge-shaped ramp inner edge 38A to apply a biasing force to the slider body intermediate portion upper face 72. This bias is transferred through the slider body intermediate portion 44 which is also contacting the second flange front end portion 86A. Thus, the downward bias causes the second sidewall back end portion 84A and the second flange back end portion 86A to move into the second position, thereby allowing the slider body intermediate portion 44 to move past the ramp 36A. Once the slider body intermediate portion 44 is past the stop ramp 36A, the blade assembly 14 has been removed and may be disposed.

Thus, similar to the front portion slider replacement assembly 80, the back portion slider replacement assembly 80A is structured to allow the second sidewall back end portion 84A and the second flange back end portion 86A to move between a first position, wherein the second sidewall back end portion 84A extends generally parallel to the first sidewall 22 and the second flange back end portion 86A extends generally parallel to the first flange 26, and a second position, wherein the second sidewall back end portion 84A is angled away from the first sidewall 22 and the second flange back end portion 86A is angled away from to the first flange 26, thereby increasing the width of the flange gap 31 at the back end of the handle member back portion 13. When the second sidewall back end portion 84A and the second flange back end portion 86A are in the normal first position, the flange gap 31 at the location of the ramp 36A is too narrow for the slider body intermediate portion 44 to pass therethrough; however, when the second sidewall back end portion 84A and the second flange back end portion 86A are in the second position, the flange gap 31 is wider. Thus, the slider body intermediate portion 44 may pass the ramp 36A and the slider 16, and therefore the blade assembly 14, may exit the channel 30. Thus, the blade assembly 14 is removable via the handle member back portion 13. In other respects, namely inserting a blade assembly, the back portion slider replacement assembly 80A operates in a manner substantially similar to the front portion slider replacement assembly 80, except, of course, the blade assembly 14 is moved forward into the channel 30.

Figure 8A:
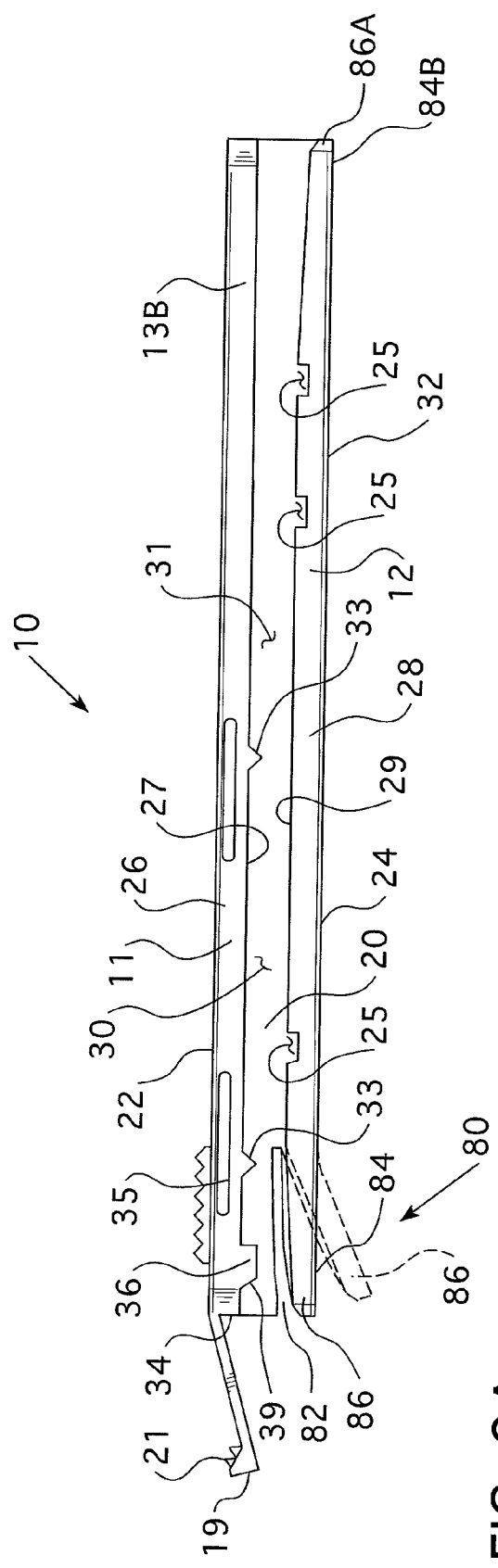
FIG. 8A is a side view of another alternate embodiment of the retractable surgical blade device with the blade assembly removed and showing the second sidewall front end portion and said second flange front end portion in a first position in solid line and the second position in ghost. It is noted that the second position of the second sidewall front end portion and said second flange front end portion is greatly exaggerated for visibility.

In another alternate embodiment, shown in FIG. 8A, the surgical blade device 10, and more specifically the handle member 12, has an open back portion 13B without a second, slider replacement assembly 80A. That is, in this embodiment the channel 30 extends the entire length of the handle member 12. Thus, the elements set forth above, namely the base wall 20, two elongated generally parallel longitudinal sidewalls 22, 24, the first, upper side wall 22 and second, lower sidewall 24, and the two elongated longitudinal flanges 26, 28, extend over the back portion 13 as well as the front portion 11.

However, unlike the alternate embodiment shown in FIG. 8, in this embodiment, the back portion 13 is simply open so that a blade assembly 14 may be removed without impediment. Accidental removal of the blade assembly 14 is substantially prevented by a plurality of locks 25, as described above. In this embodiment, the second flange 28 may be sloped at the handle member back portion 13B. That is, the second flange 28 may have a diminishing height moving from the last rearward lock 25 of the handle member 12 toward the handle member back portion 13B. This, in effect, increases the size of the gap 31 between the first and second flanges 26, 28, thereby allowing the blade assembly 14 to be removed more easily. It is noted that the second flange 28 may have a diminishing height moving from the forward most lock 25 toward the handle member front end 34. This also has the effect of increasing the size of the gap 31 between the first and second flanges 26, 28. Thus, during the insertion of a new blade assembly 14, as described above, the distance the second sidewall front end portion 84 and the second flange front end portion 86 must move to be in the second position is reduced. This, in turn, means that the force required to move these elements into the second position is reduced.

Figure 9:
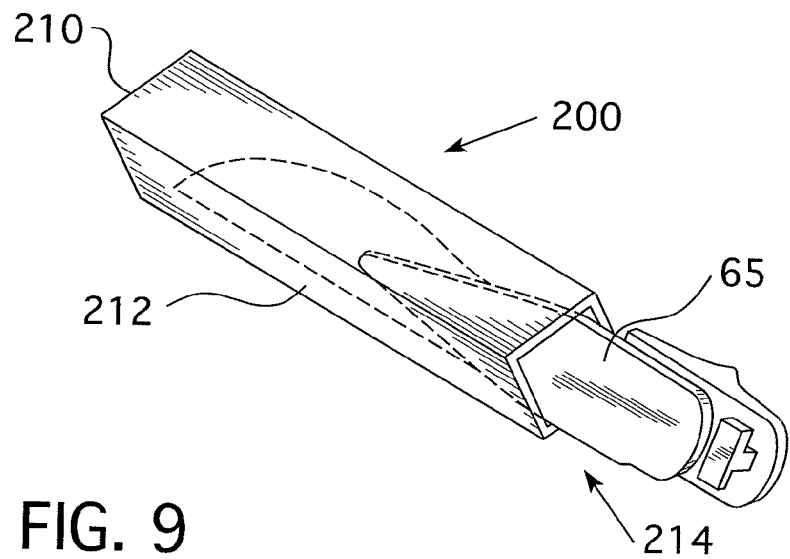
FIG. 9 is an isometric view of a blade assembly container.
Figure 10:
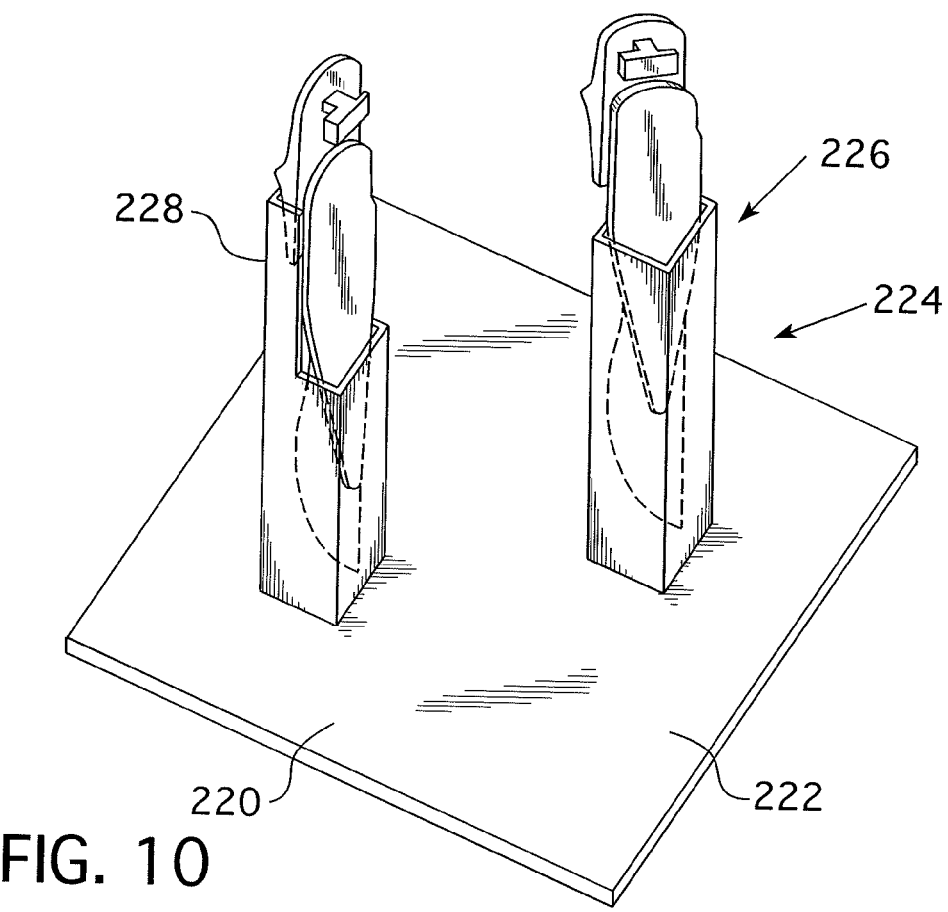
FIG. 10 is an isometric view of a blade assembly stand.
Figure 11:
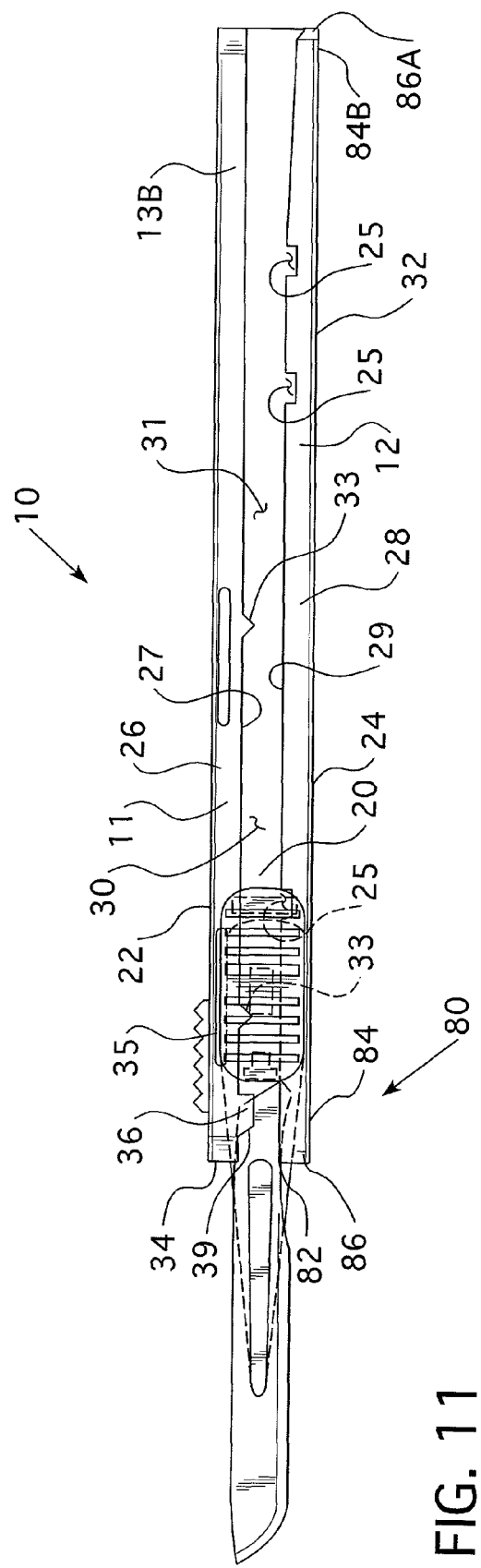
FIG. 11 is a side view of an alternate embodiment of the retractable surgical blade device.

Because there is a chance of a user injuring themselves when handling an exposed blade assembly 14, the process for insertion of a blade assembly 14 via the handle front end 34, described above, may be further improved with a blade assembly container 200 which is preferably either a cartridge 210 or a blade assembly stand 220, shown in FIGS. 9 and 10, respectively. Generally, the cartridge 210, which is preferably made of plastic, has the advantage of being able to be sterilized prior to use and may be sealed for storage. The cartridge 210 includes an elongated body 212 that defines a tube. The cartridge body 212 has at least one open end 214. The cartridge body 212 has a sufficient length to enclose at least the surgical blade lower, cutting edge 68. Thus, the cartridge body 212, and more specifically the slider body first portion 41, second portion 42 and interconnecting intermediate portion 44 are exposed. The cartridge body 212 is otherwise dimensioned to fit snugly about the slider projection 60 and preferably engages the slider body hips 66. Preferably, the blade assembly 14 cannot wobble within the cartridge 210. In this configuration, the surgical blade lower, cutting edge 68 is enclosed and the chance of a user accidentally cutting themselves while handling the blade assembly 14 within the cartridge 210 is substantially reduced. Thus, a user may simply grasp the cartridge 210 holding a blade assembly 14 and perform the insertion procedure as described above.

The blade assembly stand 220, which is preferably made from stainless steel, is capable of being sterilized and may present the user with more than one blade assembly 14 at a time. The blade assembly stand 220, preferably, has a base 222 with at least one tubular support 224 extending upwardly therefrom. Each support 224 has at least an open upper end 226 and is structured to hold a blade assembly 14. That is, surgical support staff may remove a blade assembly 14 from a sterilized package (not shown) and place each blade assembly 14 in a support 224 prior to a surgery. As with the cartridge 210, each support 224 has a sufficient length to enclose at least the surgical blade lower, cutting edge 68 while leaving the slider body 40 substantially exposed. Each support 224 is otherwise dimensioned to fit snugly about the slider projection 60 and preferably engages the slider body hips 66. It is noted that the blade assembly stand 220 would not be used to insert a blade assembly via the handle member back portion 13 as, to have the blade assembly 14 inserted in the proper direction, the blade assembly 14 would be oriented with blade 18 upwardly in the blade assembly stand 220.

To provide additional support, a support 224 may include an upward extension 228 extending from a portion of the tubular support 224. The support extension 228 is preferably a construct extending over about one hundred and eighty degrees of the perimeter of a support upper end 226. Preferably, the extension 228 is sized so as to snugly engage the upper and lower edges of the grip 49. In this configuration, each support 224 may hold a blade assembly 14 in a substantially stationary position. That is, the blade assembly 14 is substantially resistant to wobbling in the support 224 and a user may quickly align an empty handle member 12 with the blade assembly 14 so that the blade assembly 14 may be quickly inserted. It is noted that a similar extension (not shown) may be included in the cartridge 210 described above.

As noted above, the handle member 12 is, preferably, made from a stainless steel. The rigidity of the steel is related to the length of the hinge slot 82. That is, the hinge slot 82 must have an axial length sufficient to allow the second sidewall front end portion 84 and the second flange front end portion 86 to move into the second position wherein the flange gap 31 at the handle front end 34 is wide enough to allow the slider body intermediate portion upper face 72 to pass therethough. The hinge slot 82, however, should not be so long as to allow the second sidewall front end portion 84 and the second flange front end portion 86 to accidentally move into the second position. It is noted that handle members 12 made from different materials, such as, but limited to, plastic, may have hinge slots 82 with different lengths than those identified above.

It is further noted that, with this simple design, the slider replacement assembly 80 is operable without additional components, such as, but not limited to, a bifurcated handle as disclosed in U.S. Pat. No. 5,941,892, wherein more than the blade assembly 14 must be replaced or other complicated devices that provide multiple surfaces, especially surfaces within the channel 30 but which do not define the channel 30, wherein blood may cling or close surfaces wherein blood/flesh may become trapped. That is, the channel 30 of the surgical blade device 10 does not have any surface within the channel 30 that does not define the channel 30. Such additional surfaces are not conducive to an easily sterilized instrument.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of invention which is to be given the full breadth of the claims appended and any and all equivalents thereof.

What is claimed is:

1. A retractable surgical blade device, said retractable surgical blade device comprising:
   a handle member having a base wall, opposed first and second sidewalls extending generally perpendicularly from said base wall, said first sidewall including a first flange extending generally perpendicularly therefrom, said second sidewall including a second flange extending generally perpendicular therefrom;
   said base wall, said sidewalls and said first and second flanges defining a channel extending the entire length of said handle member, each said flange having a distal edge defining a flange gap therebetween;
   said handle member having a front portion with a front end and a back portion with a back end, said channel having an opening at said handle back end;

a surgical blade assembly having a slider and a surgical blade;

said slider having a body and a projection, said slider body having a first portion, a second portion, and an interconnecting intermediate portion, said slider body defining opposed first and second longitudinal slots;

a surgical blade secured to said slider projection;

said slider being disposed in said channel with said handle first and second flanges disposed in said slider body slots with said slider body second portion disposed within said channel and said slider body intermediate portion disposed within said flange gap;

wherein said slider is structured to generally move between a withdrawn position, wherein the blade is disposed within the channel, and a cutting position, wherein the blade extends beyond the handle front end and may be used for cutting a slider replacement assembly comprising:
  a back portion hinge slot and a ramp;
  said ramp disposed on said first flange adjacent to said handle back end and extending into said flange gap, said ramp having a inner edge, said ramp inner edge being shaped as a wedge with a narrow end disposed closer to said handle front;
  said back portion hinge slot extending from said back end of the handle member back portion forwardly, said back portion hinge slot structured to allow said second sidewall back end portion and said second flange back end portion to move between a first position, wherein said second sidewall back end portion extends generally parallel to said first sidewall and said second flange back end portion extends generally parallel to said first flange, and a second position, wherein said second sidewall back end portion is angled away from said first sidewall and said second flange back end portion is angled away from said first flange thereby increasing the flange gap at said handle back end; and
  wherein, when said second sidewall back end portion and said second flange back end portion are in said second position, said flange gap at said handle back end is sufficiently wide to allow said slider body to move past said ramp and exit said channel.

2. The slider replacement assembly of claim 1 wherein said slider body intermediate portion has a front face, an upper face, and a lower face, and wherein:
  when said blade assembly is disposed within said channel at said handle member back portion and said slider is moved rearwardly so that said slider engages said ramp said back portion hinge slot is structured to be responsive to a biasing force applied to said slider body upper face; and
  whereby, when a biasing force is applied to said slider body upper face, said second sidewall back end portion and said second flange back end portion are moved into said second position.

3. The slider replacement assembly of claim 2 wherein:
said ramp has a outer edge, said ramp outer edge being shaped as a wedge with the narrow end disposed at the back end of the handle member back portion; and
wherein, when said blade assembly is moved from a position outside of said channel to a position disposed in said channel via said opening at said handle back end, and said slider body intermediate portion is moved into said flange gap, as said slider body intermediate portion passes said handle back end, said slider body intermediate portion upper face engages said ramp wedge-shaped stop outer edge and said slider body intermediate portion lower face engages said second flange front end portion, thereby causing said second sidewall front end portion and said second flange front end portion to be moved into said second position.

4. The slider replacement assembly of claim 3 wherein said slider intermediate portion includes a rearward extension, said slider intermediate portion rearward extension being wedge shaped and structured to engage said ramp inner edge.

5. The slider replacement assembly of claim 1 wherein said slider replacement assembly further includes:
  a front portion hinge slot and a stop; said stop disposed on said first flange adjacent to said handle front end and extending into said flange gap, said stop having a inner edge, said stop inner edge extending generally perpendicular to the first flange distal interior edge, said stop inner edge structured to engage said slider body when said slider is at said handle front end, whereby said engagement of said slider body and said stop prevents said slider from exiting said channel;
  said front portion hinge extending from said front end of the handle member front portion rearwardly, said front portion hinge slot structured to allow said second sidewall front end portion and said second flange front end portion to move between a first position, wherein said second sidewall front end portion extends generally parallel to said first sidewall and said second flange front end portion extends generally parallel to said first flange, and a second position, wherein said second sidewall front end portion is angled away from said first sidewall and said second flange front end portion is angled away from said first flange thereby increasing the flange gap at said handle front end; and
  wherein, when said second sidewall front end portion and said second flange front end portion are in said second position, said flange gap at said handle front end is sufficiently wide to allow said slider body to move past said stop and exit said channel.

6. The slider replacement assembly of claim 5 wherein said blade has a blunt upper edge and, wherein:
  when said blade assembly is disposed within said channel and said slider is moved to said cutting position wherein said blade is exposed, said front portion hinge slot is structured to be responsive to a biasing force applied to said blade upper edge; and
  whereby, when a biasing force is applied to said blade upper edge, said second sidewall front end portion and said second flange front end portion are moved into said second position.

7. The slider replacement assembly of claim 6 wherein, said slider body intermediate portion has a front face, an upper face, and a lower face, and wherein:
  said stop has a outer edge, said stop outer edge being shaped as a wedge with a narrow end disposed closer to said handle front end; and
  wherein, when said blade assembly is moved from a position outside of said channel to a position disposed in said channel via said opening at said handle front end, and said slider body intermediate portion is moved into said flange gap, as said slider body intermediate portion passes said handle front end, said slider body intermediate portion upper face engages said wedge-shaped stop outer edge and said slider body intermediate portion lower face engages said second flange front end portion, thereby causing said second sidewall front end portion and said second flange front end portion to be moved into said second position.

8. A retractable surgical blade device comprising:
- a handle member having a base wall, opposed first and second sidewalls extending generally perpendicularly from said base wall, said first sidewall including a first flange extending generally perpendicularly therefrom, said second sidewall including a second flange extending generally perpendicular therefrom;
- said base wall, said sidewalls and said first and second flanges defining a channel extending the entire length of said handle member, each said flange having a distal edge defining a flange gap therebetween;
- said handle member having a front portion with a front end and a back portion with a back end, said channel having an opening at said handle back end;
- a surgical blade assembly having a slider and a surgical blade;
- said slider having a body and a projection, said slider body having a first portion, a second portion, and an interconnecting intermediate portion, said slider body defining opposed first and second longitudinal slots;
- said surgical blade secured to said slider projection;
- said slider being disposed in said channel with said handle first and second flanges disposed in said slider body slots with said slider body second portion disposed within said channel and said slider body intermediate portion disposed within said flange gap;
- a slider replacement assembly consisting of:
  - a back portion hinge slot and a ramp;
  - said ramp disposed on said first flange adjacent to said handle back end and extending into said flange gap, said ramp having a inner edge, said ramp inner edge being shaped as a wedge with a narrow end disposed closer to said handle front;
  - said back portion hinge slot extending from said back end of the handle member back portion forwardly, said back portion hinge slot structured to allow said second sidewall back end portion and said second flange back end portion to move between a first position, wherein said second sidewall back end portion extends generally parallel to said first sidewall and said second flange back end portion extends generally parallel to said first flange, and a second position, wherein said second sidewall back end portion is angled away from said first sidewall and said second flange back end portion is angled away from said first flange thereby increasing the flange gap at said handle back end; and
- wherein, when said second sidewall back end portion and said second flange back end portion are in said second position, said flange gap at said handle back end is sufficiently wide to allow said slider body to move past said ramp and exit said channel.

9. The slider replacement assembly of claim 8 wherein said slider body intermediate portion has a front face, an upper face, and a lower face, and wherein:
- when said blade assembly is disposed within said channel at said handle member back portion and said slider is moved rearwardly so that said slider engages said ramp said back portion hinge slot is structured to be responsive to a biasing force applied to said slider body upper face; and
- whereby, when a biasing force is applied to said slider body upper face, said second sidewall back end portion and said second flange back end portion are moved into said second position.

10. The slider replacement assembly of claim 9 wherein:
- said ramp has a outer edge, said ramp outer edge being shaped as a wedge with the narrow end disposed at the back end of the handle member back portion; and
- wherein, when said blade assembly is moved from a position outside of said channel to a position disposed in said channel via said opening at said handle back end, and said slider body intermediate portion is moved into said flange gap, as said slider body intermediate portion passes said handle back end, said slider body intermediate portion upper face engages said ramp wedge-shaped stop outer edge and said slider body intermediate portion lower face engages said second flange front end portion, thereby causing said second sidewall front end portion and said second flange front end portion to be moved into said second position.

11. The slider replacement assembly of claim 9 wherein said slider replacement assembly further includes:
- a front portion hinge slot and a stop; said stop disposed on said first flange adjacent to said handle front end and extending into said flange gap, said stop having a inner edge, said stop inner edge extending generally perpendicular to the first flange distal interior edge, said stop inner edge structured to engage said slider body when said slider is at said handle front end, whereby said engagement of said slider body and said stop prevents said slider from exiting said channel;
- said front portion hinge extending from said front end of the handle member front portion rearwardly, said front portion hinge slot structured to allow said second sidewall front end portion and said second flange front end portion to move between a first position, wherein said second sidewall front end portion extends generally parallel to said first sidewall and said second flange front end portion extends generally parallel to said first flange, and a second position, wherein said second sidewall front end portion is angled away from said first sidewall and said second flange front end portion is angled away from said first flange thereby increasing the flange gap at said handle front end; and
- wherein, when said second sidewall front end portion and said second flange front end portion are in said second position, said flange gap at said handle front end is sufficiently wide to allow said slider body to move past said stop and exit said channel.

12. A retractable surgical blade device comprising:
- a handle member having a base wall, opposed first and second sidewalls extending generally perpendicularly from said base wall, said first sidewall including a first flange extending generally perpendicularly therefrom, said second sidewall including a second flange extending generally perpendicular therefrom;
- said handle member having a front portion and a back portion, said front portion having a front end, said back portion having a back end;
- said base wall, said sidewalls and said first and second flanges defining a channel extending the entire length of said handle member;
- said channel having an opening at said handle front end and said handle back end;
- each said flange having a distal edge defining a flange gap therebetween;
- a surgical blade assembly having a slider and a surgical blade;
- said slider having a body and a projection;

said slider body having a first portion, a second portion and an interconnecting intermediate portion, said slider body defining opposed first and second longitudinal slots;

said surgical blade secured to said slider projection;

said slider being disposed in said channel with said handle first and second flanges disposed in said slider body slots with said slider body second portion disposed within said channel and said slider body intermediate portion disposed within said flange gap;

wherein said slider is structured to generally move between a withdrawn position, wherein the surgical blade is disposed within the channel, and a cutting position, wherein the surgical blade extends through said opening at said handle front end and may be used for cutting;

a slider replacement assembly including a back portion hinge slot and a ramp;

said ramp disposed on said first flange adjacent to said handle back end and extending into said flange gap, said ramp having a inner edge, said ramp inner edge being shaped as a wedge with a narrow end disposed closer to said handle front;

said back portion hinge slot extending from said back end of the handle member back portion forwardly, said back portion hinge slot structured to allow said second sidewall back end portion and said second flange back end portion to move between a first position, wherein said second sidewall back end portion extends generally parallel to said first sidewall and said second flange back end portion extends generally parallel to said first flange, and a second position, wherein said second sidewall back end portion is angled away from said first sidewall and said second flange back end portion is angled away from said first flange thereby increasing the flange gap at said handle back end; and wherein, when said second sidewall back end portion and said second flange back end portion are in said second position, said flange gap at said handle back end is sufficiently wide to allow said slider body to move past said ramp and exit said channel.

13. The retractable surgical blade device of claim 12 wherein said slider body intermediate portion has a front face, an upper face, and a lower face, and wherein:

when said blade assembly is disposed within said channel at said handle member back portion and said slider is moved rearwardly so that said slider engages said ramp said back portion hinge slot is structured to be responsive to a biasing force applied to said slider body upper face; and whereby, when a biasing force is applied to said slider body upper face, said second sidewall back end portion and said second flange back end portion are moved into said second position.

14. The retractable surgical blade device of claim 13 wherein:

said ramp has a outer edge, said ramp outer edge being shaped as a wedge with the narrow end disposed at the back end of the handle member back portion; and wherein, when said blade assembly is moved from a position outside of said channel to a position disposed in said channel via said opening at said handle back end, and said slider body intermediate portion is moved into said flange gap, as said slider body intermediate portion passes said handle back end, said slider body intermediate portion upper face engages said ramp wedge-shaped stop outer edge and said slider body intermediate portion lower face engages said second flange front end portion, thereby causing said second sidewall front end portion and said second flange front end portion to be moved into said second position.

15. The retractable surgical blade device of claim 14 wherein said slider intermediate portion includes a rearward extension, said slider intermediate portion rearward extension being wedge shaped and structured to engage said ramp inner edge.

16. The retractable surgical blade device of claim 12 wherein said slider replacement assembly further includes:

a front portion hinge slot and a stop; said stop disposed on said first flange adjacent to said handle front end and extending into said flange gap, said stop having a inner edge, said stop inner edge extending generally perpendicular to the first flange distal interior edge, said stop inner edge structured to engage said slider body when said slider is at said handle front end, whereby said engagement of said slider body and said stop prevents said slider from exiting said channel;

said front portion hinge extending from said front end of the handle member front portion rearwardly, said front portion hinge slot structured to allow said second sidewall front end portion and said second flange front end portion to move between a first position, wherein said second sidewall front end portion extends generally parallel to said first sidewall and said second flange front end portion extends generally parallel to said first flange, and a second position, wherein said second sidewall front end portion is angled away from said first sidewall and said second flange front end portion is angled away from said first flange thereby increasing the flange gap at said handle front end; and wherein, when said second sidewall front end portion and said second flange front end portion are in said second position, said flange gap at said handle front end is sufficiently wide to allow said slider body to move past said stop and exit said channel.

17. The retractable surgical blade device of claim 16 wherein said blade has a blunt upper edge and, wherein:

when said blade assembly is disposed within said channel and said slider is moved to said cutting position wherein said blade is exposed, said front portion hinge slot is structured to be responsive to a biasing force applied to said blade upper edge; and whereby, when a biasing force is applied to said blade upper edge, said second sidewall front end portion and said second flange front end portion are moved into said second position.

18. The retractable surgical blade device of claim 17 wherein, said slider body intermediate portion has a front face, an upper face, and a lower face, and wherein:

said stop has a outer edge, said stop outer edge being shaped as a wedge with a narrow end disposed closer to said handle front end; and wherein, when said blade assembly is moved from a position outside of said channel to a position disposed in said channel via said opening at said handle front end, and said slider body intermediate portion is moved into said flange gap, as said slider body intermediate portion passes said handle front end, said slider body intermediate portion upper face engages said wedge-shaped stop outer edge and said slider body intermediate portion lower face engages said second flange front end portion, thereby causing said second sidewall front end portion and said second flange front end portion to be moved into said second position.

19. The retractable surgical blade device of claim 12 wherein:
   said upper side wall at said handle member front portion includes a longitudinal extension;
   said handle member extension being cantilevered over the path of travel of the blade assembly;
   whereby a user may flex said extension downwardly thereby moving said second sidewall front end portion and said second flange front end portion into said second position.

* * * * *

UNITED STATES PATENT AND TRADEMARK OFFICE
CERTIFICATE OF CORRECTION

| | | |
|---|---|---|
| PATENT NO. | : 8,181,352 B1 | Page 1 of 1 |
| APPLICATION NO. | : 12/326944 | |
| DATED | : May 22, 2012 | |
| INVENTOR(S) | : Howard L. Shackelford, Sr. et al. | |

It is certified that error appears in the above-identified patent and that said Letters Patent is hereby corrected as shown below:

Title page, first column, item (56); U.S. PATENT DOCUMENTS, "Krat" should read --Kratz--.

Column 13, line 17, "cutting" should read --cutting;--.

Signed and Sealed this
Twenty-eighth Day of August, 2012

David J. Kappos
*Director of the United States Patent and Trademark Office*